(12) United States Patent
Clayborne et al.

(10) Patent No.: US 10,980,676 B2
(45) Date of Patent: *Apr. 20, 2021

(54) NASAL COMPRESSION DEVICE

(71) Applicant: Emergency Medical Innovation LLC, Laurel, MD (US)

(72) Inventors: Elizabeth P. Clayborne, Fairfax, VA (US); Neal K. Sikka, Vienna, VA (US); Romil Patel, Jamestown, RI (US)

(73) Assignee: Emergency Medical Innovation LLC, Highland, MD (US)

( * ) Notice: Subject to any disclaimer, the term of this patent is extended or adjusted under 35 U.S.C. 154(b) by 103 days.

This patent is subject to a terminal disclaimer.

(21) Appl. No.: 16/265,469

(22) Filed: Feb. 1, 2019

(65) Prior Publication Data

US 2019/0167486 A1 Jun. 6, 2019

Related U.S. Application Data

(63) Continuation of application No. 15/096,819, filed on Apr. 12, 2016, now Pat. No. 10,195,088.

(Continued)

(51) Int. Cl.
*A61F 13/12* (2006.01)
*A61F 7/10* (2006.01)
(Continued)

(52) U.S. Cl.
CPC .............. *A61F 13/126* (2013.01); *A61F 7/10* (2013.01); *A61F 2007/0006* (2013.01); *A61F 2013/0028* (2013.01); *A61F 2013/00285* (2013.01)

(58) Field of Classification Search
CPC .............. A61B 17/12104; A61B 17/24; A61B 2017/12004; A61B 17/1227; A61B 9/06;
(Continued)

(56) References Cited

U.S. PATENT DOCUMENTS

| 598,467 A | 2/1898 | Carence |
|---|---|---|
| 675,275 A | 5/1901 | Gunning |

(Continued)

FOREIGN PATENT DOCUMENTS

| GB | 695963 A | 8/1953 |
|---|---|---|
| GB | 816887 A | 7/1959 |

(Continued)

OTHER PUBLICATIONS

"The Bleed Freeze Solution," Bleed Freeze: 2015 GW Business Plan Competition Final Presentation, Youtube, published Jul. 2, 2015, 1 page.

(Continued)

*Primary Examiner* — Scott J Medway
(74) *Attorney, Agent, or Firm* — Blank Rome LLP

(57) ABSTRACT

A nose compression device for treating a nosebleed of a person. The device includes a wire frame having a straight middle section and two end sections angled with respect to the middle section. The device also has a body attached to the wire frame, and two nasal sponges attached to the body for insertion into the person's nasal passages. The end sections are wider than the user's nose, and the device is slid upward on the user's face so that the nasal sponges enter the user's nasal passages. The end sections are then bent inward to a pinch position where they pinch the upper lateral side surfaces of the user's nose. The nasal sponges can be pre-treated with medication to further stop the nosebleed. Ice pack may also be provided that extends over the compression device. The combination of compression, medication, and cooling facilitate treatment of the nosebleed.

32 Claims, 12 Drawing Sheets

Related U.S. Application Data

(60) Provisional application No. 62/146,697, filed on Apr. 13, 2015.

(51) Int. Cl.
 *A61F 13/00* (2006.01)
 *A61F 7/00* (2006.01)

(58) Field of Classification Search
 CPC ................ A61F 13/126; A61F 13/2005; A61F 2007/0006; A61F 2013/00476; A61F 13/20; A61F 13/2022; A61F 2013/00463; A61M 2210/0618
 See application file for complete search history.

(56) References Cited

U.S. PATENT DOCUMENTS

| | | | |
|---|---|---|---|
| 1,520,930 | A | 12/1924 | Calhoun |
| 2,215,126 | A | 9/1940 | McMillian |
| 2,681,652 | A | 6/1954 | Laxton |
| 3,349,771 | A | 10/1967 | Baer |
| 3,463,149 | A | 8/1969 | Albu |
| 3,643,660 | A | 2/1972 | Hudson |
| 3,747,597 | A | 7/1973 | Olivera |
| 3,802,431 | A | 4/1974 | Farr |
| 4,231,360 | A | 11/1980 | Zloczysti |
| 4,457,756 | A | 7/1984 | Kern et al. |
| 4,774,935 | A | 10/1988 | Aronsohn |
| 4,859,360 | A | 8/1989 | Suzuki |
| 5,383,891 | A | 1/1995 | Walker |
| 5,584,822 | A | 12/1996 | Lively et al. |
| 5,752,511 | A | 5/1998 | Simmons |
| 5,887,437 | A | 3/1999 | Maxim |
| 5,899,918 | A | 5/1999 | Knott et al. |
| 6,666,211 | B1 | 12/2003 | Awoniyi |
| D494,671 | S | 8/2004 | Chiang |
| 2,015,617 | A1 | 12/2005 | Shippert |
| 7,294,138 | B2 | 11/2007 | Shippert |
| 7,506,649 | B2 | 3/2009 | Doshi |
| 8,161,971 | B2 | 4/2012 | Jaffe |
| 8,240,309 | B2 | 8/2012 | Doshi |
| 8,303,619 | B2 | 11/2012 | DeCrescenzo et al. |
| 8,403,954 | B2 | 3/2013 | Santin |
| 8,974,486 | B2 | 3/2015 | Kotler |
| 9,730,830 | B2 | 8/2017 | Foley |
| 10,058,732 | B2 | 8/2018 | Ghosh |
| 2002/0124844 | A1 | 9/2002 | Chiang |
| 2004/0010283 | A1 | 1/2004 | Buzard |
| 2005/0187502 | A1 | 8/2005 | Krempel |
| 2006/0206120 | A1 | 9/2006 | Clawson |
| 2006/0287699 | A1 | 12/2006 | Riedle |
| 2009/0007919 | A1 | 1/2009 | Dolezal |
| 2009/0149772 | A1 | 6/2009 | MacDonald et al. |
| 2009/0299405 | A1 | 12/2009 | DeCrescenzo et al. |
| 2010/0252040 | A1 | 10/2010 | Kapust |
| 2013/0092173 | A1 | 4/2013 | Alexander |
| 2013/0245584 | A1 | 9/2013 | Krasikoff |
| 2016/0030523 | A1 | 2/2016 | Husain |
| 2016/0220251 | A1 | 8/2016 | Ghosh |
| 2016/0235953 | A1 | 8/2016 | Hsu |
| 2016/0296378 | A1 | 10/2016 | Phillips et al. |
| 2016/0324679 | A1 | 11/2016 | Khan |

FOREIGN PATENT DOCUMENTS

| | | |
|---|---|---|
| GB | 1511634 | 5/1978 |
| GB | 2363575 A | 1/2002 |
| WO | WO-201408022 A1 | 5/2014 |

OTHER PUBLICATIONS

"NoseAid, first aid for nosebleeds," Clever Products LLC, 2005, 6 pages.
International Search Report and Written Opinion issued in PCT/US17/18141 dated May 10, 2017.
"Rapid Rhino Controls Epistaxis", ArthroCare ENT, Rapid Rhino, 2 pages.
"NoseBudd helps to stop nosebleeds cold!™", Nosebudd, 2 pages.
"What is merocel material?", 1 page.

NASAL COMPRESSION DEVICE

RELATED APPLICATIONS

This application is a continuation of U.S. patent application Ser. No. 15/096,819, filed Apr. 12, 2016. U.S. Pat. No. 10,195,088, which claims the benefit of U.S. Provisional Application No. 62/146,697, filed Apr. 13, 2015. The entire contents of these applications are incorporated herein by reference.

BACKGROUND OF THE INVENTION

Field of the Invention

The present invention relates to nasal compression devices. More particularly, the present invention relates to a nasal compression clip to treat nosebleeds.

Background of the Related Art

Sixty percent of people will experience a nosebleed in their lifetime. In the United States, nosebleeds account for approximately 1 in 200 emergency department visits, which is over 500,000 visits to the emergency room annually of which nearly 90% safely sent home. Nosebleeds are very messy, bloody, anxiety provoking experiences that could be easily managed at home if treated appropriately. Epistaxis, the medical term for nosebleed, is one of the most common ear, nose, and throat emergencies. Epistaxis has a bimodal age distribution, with most cases in children 2-10 years old and adults 50-80 years old. Certain high-risk groups, such as the elderly, require rapid intervention to stem bleeding and prevent further complications.

Nosebleeds are commonly mismanaged when they first begin. One common mistake in treating nosebleeds relates to improper compression. Nosebleeds should be treated by applying appropriate pressure to the soft side walls of the nose, for 10 to 15 minutes without interruption, and positioning the head slightly forward. While this sounds simple, it is hard to do. Another common mistake is inadequate compression time. Nosebleeds need compression for 10 to 15 minutes without interruption. Due to arm fatigue, these steps are hard to do consistently.

Medications can be used to constrict vessels to help stop bleeding. However, there is little education or awareness of how, when and what medications can be used. At home, children and elderly may easily tire, forget, or not understand these steps for successful nosebleed rescue.

SUMMARY OF THE INVENTION

Accordingly, it is an object of the invention to provide a device that treats nosebleeds. It is another object of the invention to provide a device that treats nosebleeds by applying a compression force against the lateral side surfaces of the user's nose. It is another object of the invention to provide a device that treats nosebleeds by inserting a sponge inside the user's nasal passage. It is another object of the invention to provide a device that treats nosebleeds by applying a compression force against the lateral side surfaces of the user's nose at the same time it inserts a sponge inside the user's nasal passage. It is a further object of the invention to provide a nose compression device that can be used hands-free and that does not obstruct the user's mouth and/or eyes.

A nose compression device for treating a nosebleed of a person. The device includes a wire frame having a straight middle section and two end sections angled with respect to the middle section. The device also has a body attached to the wire frame, and two nasal sponges attached to the body for insertion into the person's nasal passages. The end sections are biased inward so that they are at an acute angle with respect to the middle section. The end sections are spread apart to be wider than the user's nose, and the device is slid upward on the user's face so that the nasal sponges enter the user's nasal passages. The end sections are then released so that they return inward to a pinch position where they pinch the upper lateral side surfaces of the user's nose. The nasal sponges can be pre-treated with medication and/or materials to further stop the nosebleed.

These and other objects of the invention, as well as many of the intended advantages thereof, will become more readily apparent when reference is made to the following description, taken in conjunction with the accompanying drawings.

DETAILED DESCRIPTION OF THE PREFERRED EMBODIMENTS

Figure 1:
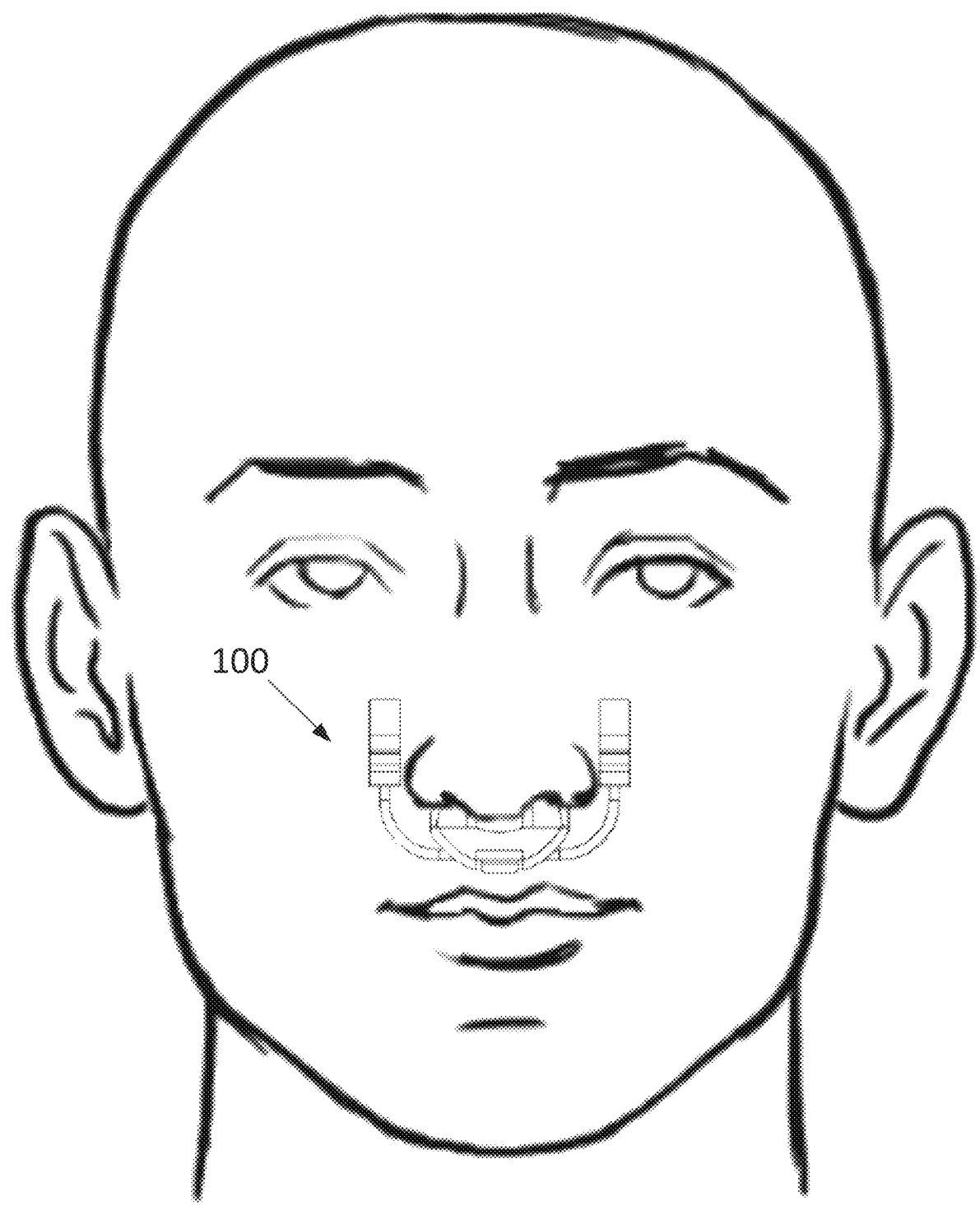
FIG. 1 is a top view of the nasal compression device positioned on a user in accordance with an embodiment of the invention.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in similar manner to accomplish a similar purpose. Several preferred embodiments of the invention are described for illustrative purposes, it being understood that the invention may be embodied in other forms not specifically shown in the drawings.

Figure 2:
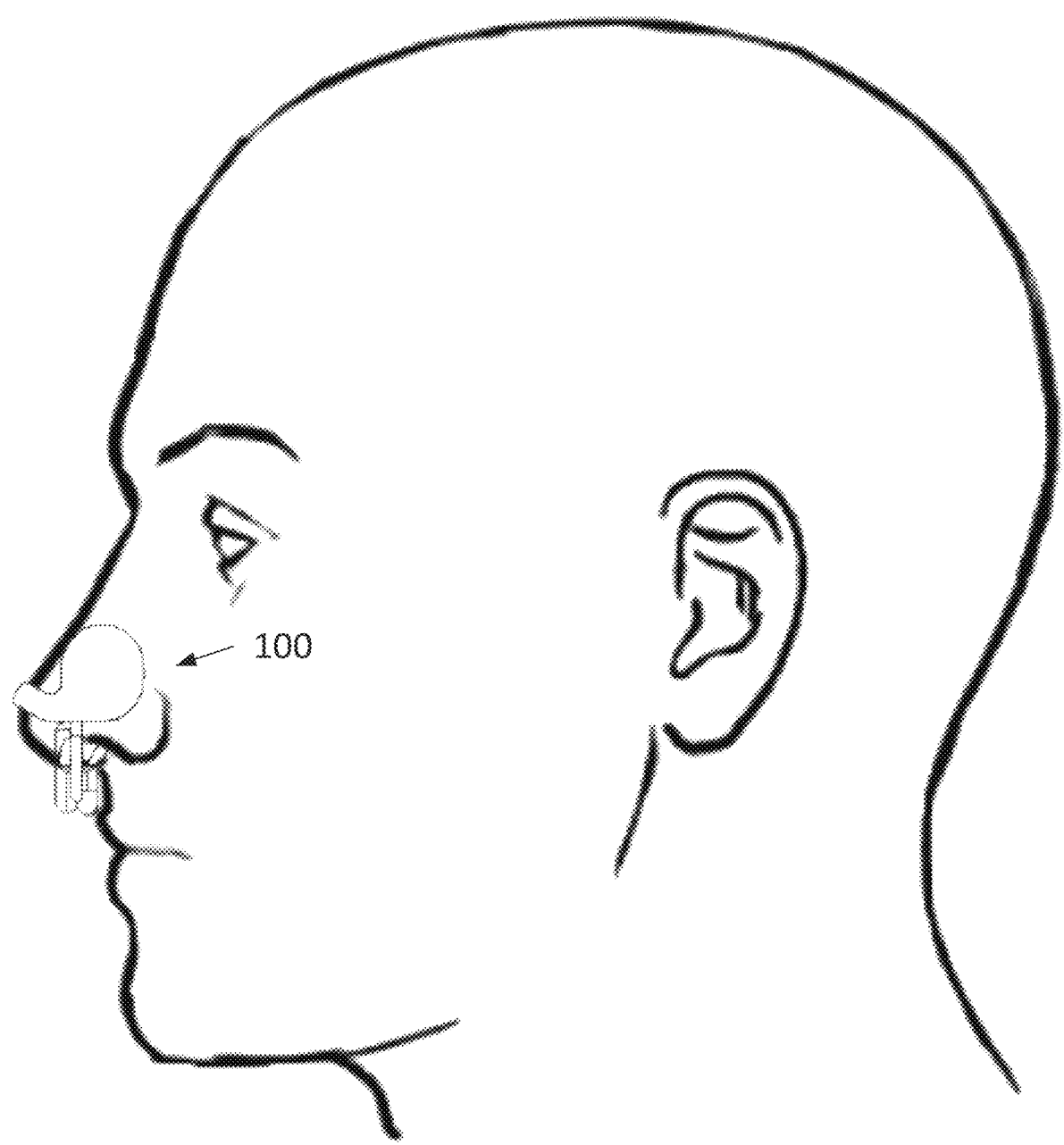
FIG. 2 is a side view of the nasal compression device positioned on a user.
Figure 3A:
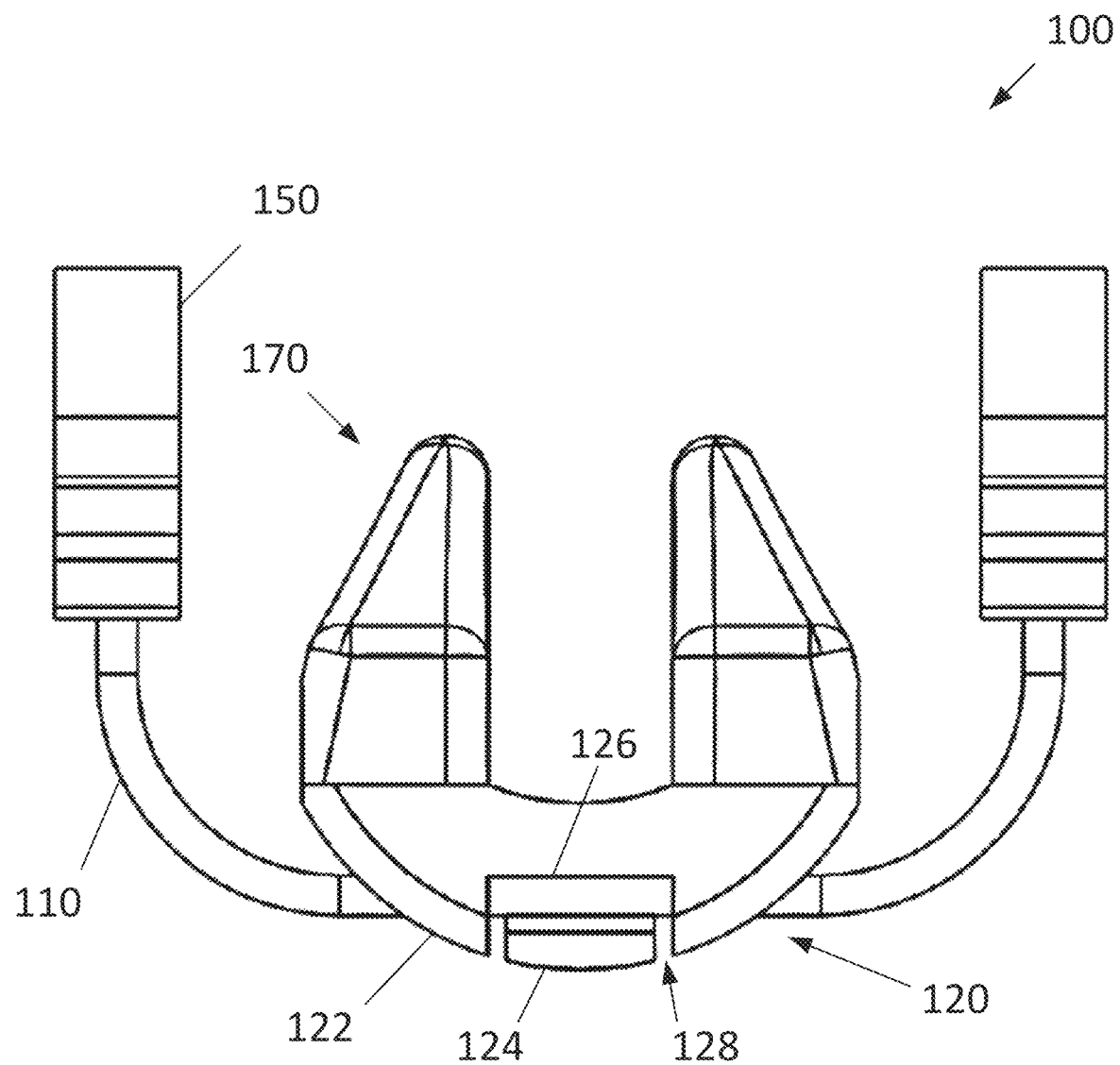
FIG. 3(a) is a top view of the nasal compression device in an open position.
Figure 4:
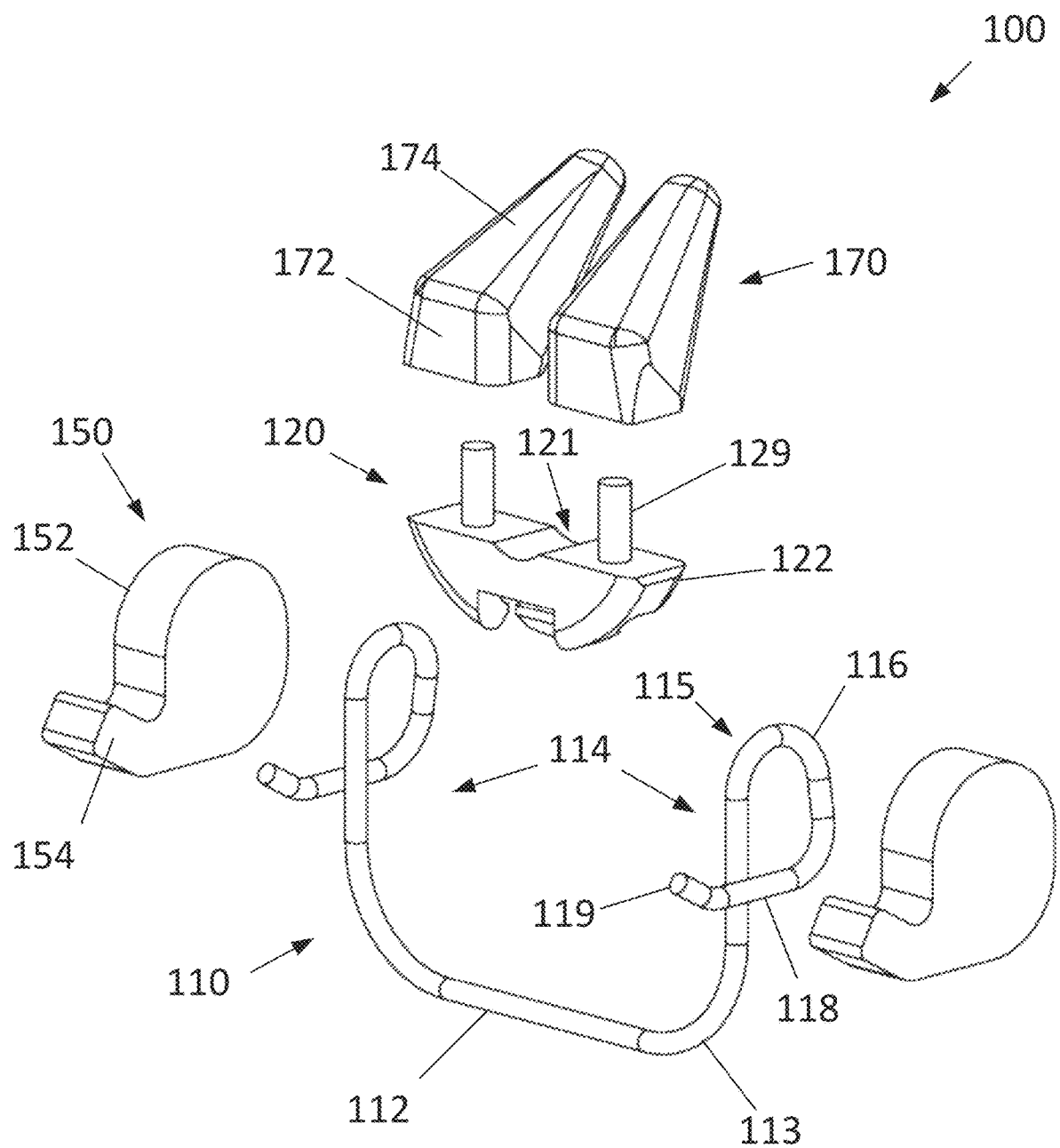
FIG. 4 is an exploded view of the nasal compression device.
Figure 5:
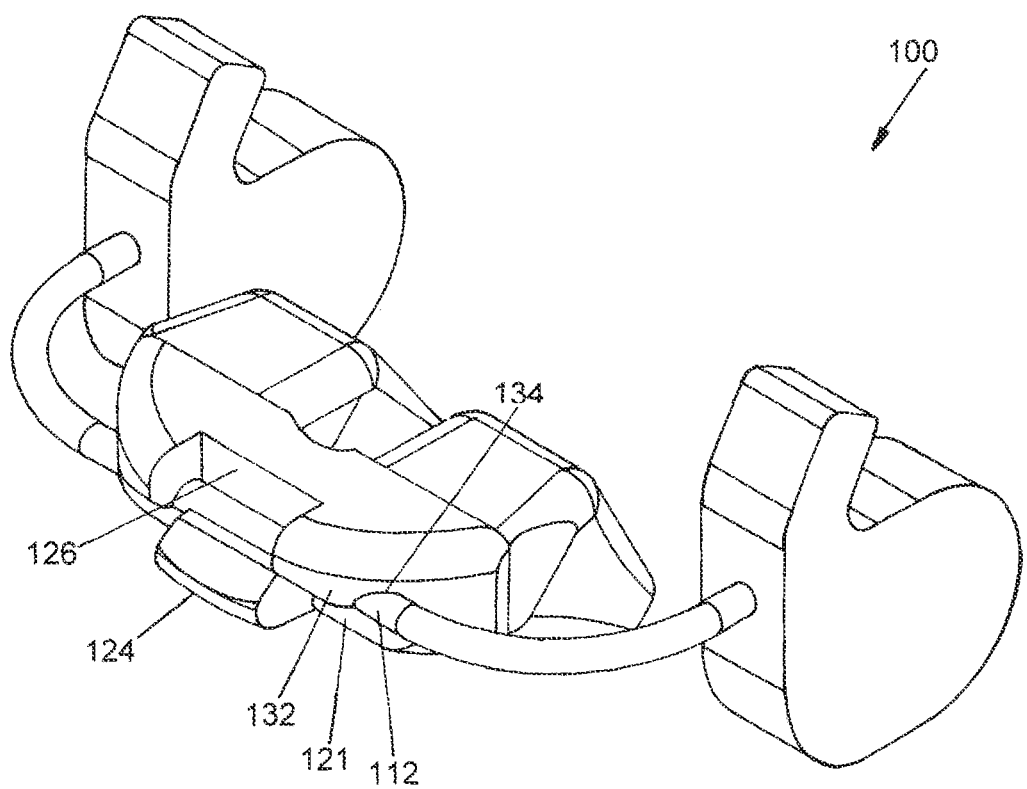
FIG. 5 is a perspective view of the nasal compression device.

Turning to the drawings. FIGS. 1-7 show a nasal compression device 100 in accordance with one illustrative non-limiting example of the invention. As best shown in FIGS. 1-2, the device 100 may be a clip that is designed to treat anterior epistaxis or nosebleeds. Referring to FIGS. 3-5, the device 100 may include a frame member 110, an adaptor or body portion 120, external pressure members 150, and internal pressure members 170.

Frame Member 110

As best shown in FIG. 4, the frame member 110 may be, for instance, an elongated flexible wire. The wire 110 may have a central portion 112, two intermediate or side portions 114, and a distal end portion 115. Each side portion 114 extends outward from an opposite end of the central portion 112, so that the central portion 112 is positioned between the two side portions 114. The central portion 112 and each side portion 114 are substantially straight, and have a curved corner or bend 113 therebetween. The side portions 114 are flexible and can be moved. In a rest position, the side portions 114 are positioned outwardly, as shown in FIGS. 1, 3(a), 4-7. In this manner, the central portion 112 and side portions 114 form a general U-shape.

Figure 3B:
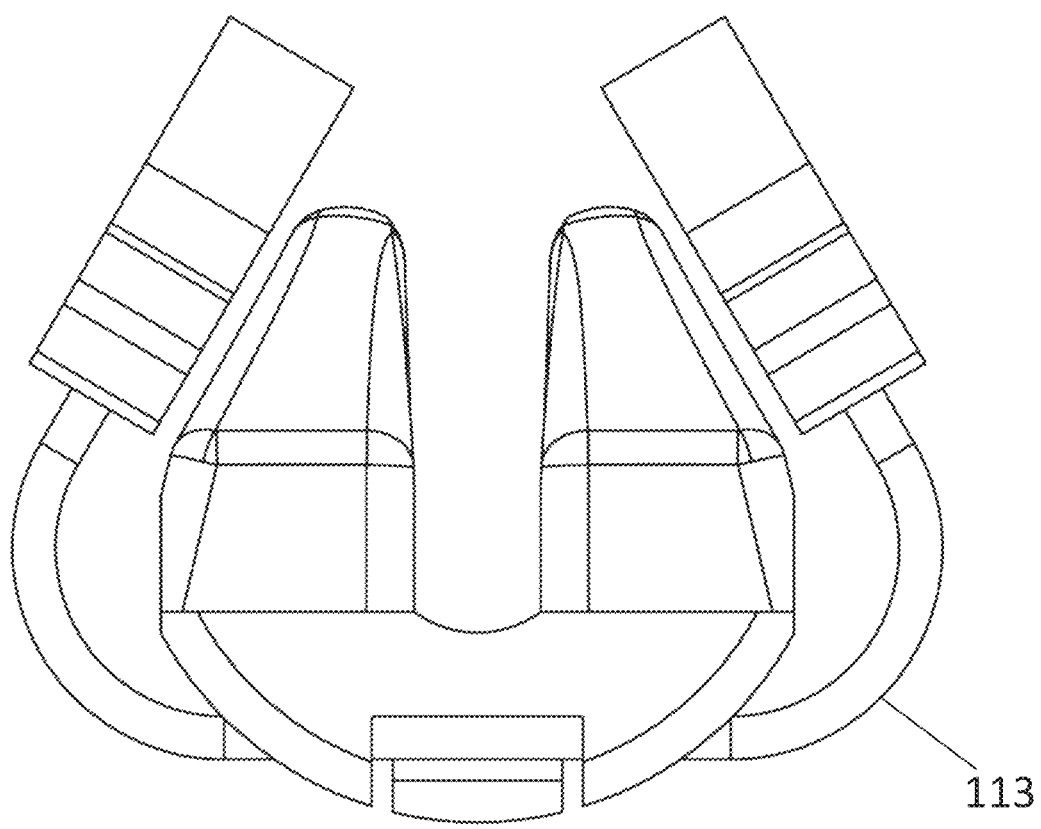
FIG. 3(b) is a top view of the nasal compression device in a closed or pinch position.
Figure 3C:
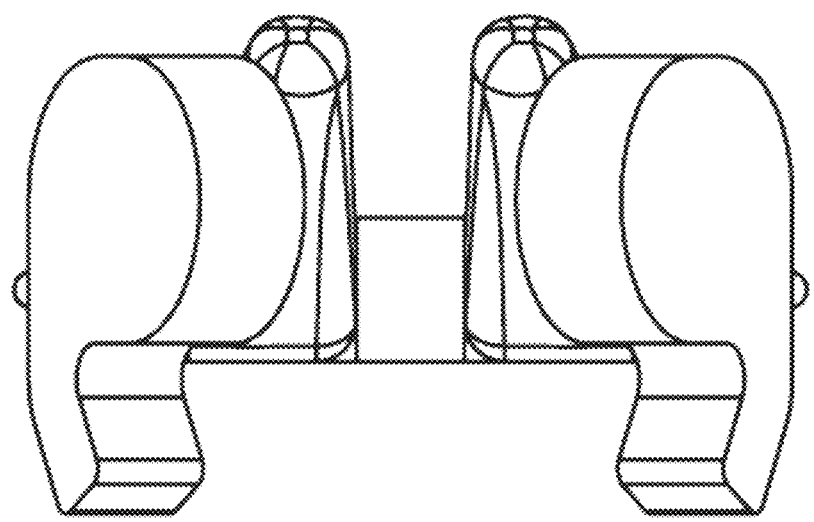
FIG. 3(c) is a front view of the nasal compression device in the closed position.

However, one or both of the side portions 114 can be moved inwardly by the user into a closed position or a pinch position, which is shown in FIGS. 3(b), 3(c). For instance, the user may simultaneously press inwardly on the side portions 114 and/or on the outside of the external pressure members 150 to bend the corners 113 so that the distal ends 115 of the side portions 114 move inward toward each other and toward the internal pressure members 170, so that each side portion 114 is at an acute angle with respect to the central portion 112. However, the distal ends 115 do not touch one another. The side portions 114 may retain the inward shape until changed by the user.

The distal end portion 115 can optionally be configured to provide a structure that may readily be coupled with a respective external pressure member 150. For instance, the distal end portion 115 may form a reverse U-shaped bend 116 at the distal end of the side portions 114. The reverse bend 116 leads to a cross-member that curves back and crosses the side portion 114, such that the reverse bend 116 and cross-member 118 substantially form a closed oblong shape when viewed from the side. The cross-member 118 is separated from the side portion 114 so that they do not touch one another and so the external pressure member 150 can be readily fitted to the distal end portion 115 without obstruction by the side portion 114. As shown, the very distal end 119 of the distal end portion 114 may further optionally be slightly bent or offset (upward in the embodiment of FIG. 4) to more reliably couple with the external pressure member 150.

The entire frame member 110 (including the central portion, side portions 14, and distal end portion 115) is formed as a single unitary and continuous member. The frame 110 and the inward tension may be formed in any suitable manner, including molded shape, by spring, by shape memory polymer or by metal. Preferably, however, the frame member 110 pinches the nasal pads to allow for constant, appropriate and effective pressure on the outer nose. Still in further embodiments, the frame 110 can be a shape memory polymer that is cold activated.

Clipping Mechanism 120

Referring to FIGS. 3 and 4, the body portion 120 of the device 100 is also shown. The body portion 120 may be formed as a clipping or attachment mechanism having a main body 122, a clip 124, and prongs 129. The main body may have a semi-circular shape with a bottom side and a top side. As best shown in FIG. 5, the attachment mechanism 120 includes a recessed portion 121 that creates a ledge 132 formed at the bottom side of the main body 122. A central cutout 126 is provided in the ledge 132. The clip 124 extends outward from the recessed portion 121 and is aligned with the cutout 126. The clip has a lip that extends upward (in the embodiment of FIGS. 5, 7), and the ledge 132 has a lip that extends downward (in FIGS. 5, 7). The clip 124 and ledge 132, and their respective lips, form a channel 134 at the bottom of the clipping mechanism 120.

Figure 6:
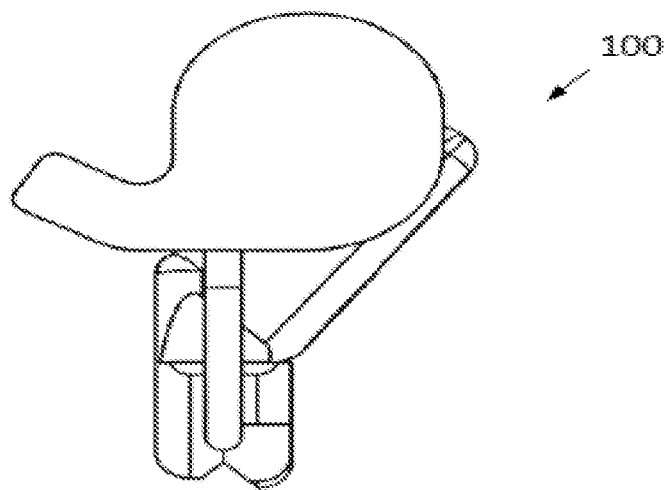
FIG. 6 is a side view of the nasal compression device.
Figure 7:
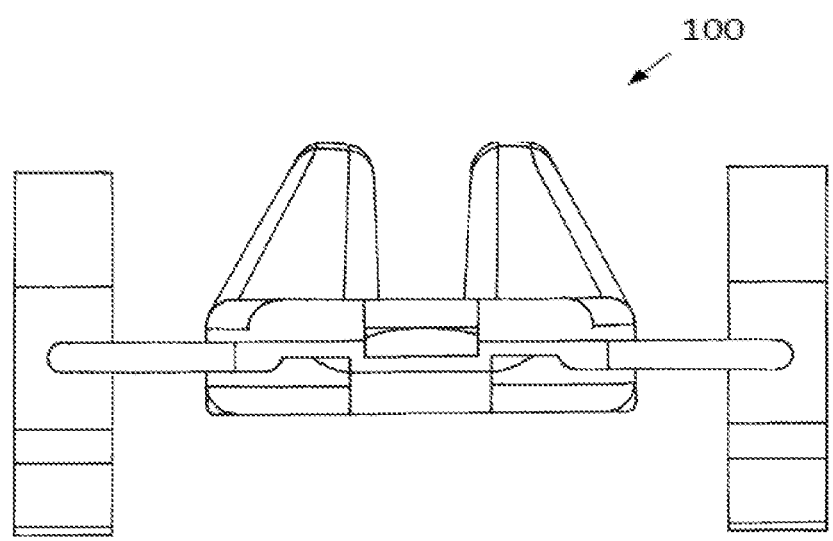
FIG. 7 is a front view of the nasal compression device.

As further illustrated in FIGS. 5-7, the clipping mechanism 120 can be removably coupled with the frame 110, such as at the central portion 112 of the frame 110. The clip 124 may have a tapered top surface and the ledge 132 can have a tapered bottom surface. The user can connect the frame 110 to the body portion 120 by pushing the frame 110 inward against the tapered surfaces. The tapered surfaces cause the clip 124 to be pushed out slightly with respect to the ledge 132 to allow the central frame portion 112 to snap into the channel 134. Once the frame 110 is coupled to the body portion 120, it remains in position. The clip is sufficiently strong to provide enough friction between the clip and the frame to prevent the body portion 120 from rotating with respect to the frame central portion 112. The body portion 120 can be removed by the user forcing the clip apart from the ledge 132 and pulling the frame 120 outward with respect to the main body 122. It will be appreciated that other suitable attachment mechanisms 120 can be provided, such as by use of a fastener, and/or adhesive. Preferably, however, the body portion 120 can be removed from the frame 110 so that different size body portion 120 or frame 110 can be provided or replaced.

As best shown in FIG. 4, a set of two prongs 129 are provided at the top surface of the main body 122. The prongs 129 are elongated and extend outward (upward in FIG. 4). The prongs are separated from each other. Each prong 129 can receive a respective one of the internal pressure members 170. A small curved recess 121 can be provided in the top surface of the main body 122 to conform to the user's nasolabial angle of the external nose. Accordingly, the body portion 120 couples the internal pressure members 170 to the frame 110. In addition, the external pressure members 150 are coupled to the frame 110. Thus, the device 100 provides both internal and external pressure members 170, 150 in a single unit. Or, the body portion 120 can be removed from the frame 110 so that the user can utilize only the internal pressure member 170 or the external pressure member 150, depending on a particular application.

The body portion 120 may preferably be made of a plastic that is rigid but allows the clip 124 to flex slightly due to the small amount of material where the clip 124 connects to the main body 122. The body portion 120 may be made from plastic polymers, metal, foam or combination materials to help with traction and comfort. The body portion 120 can be formed as a discrete member, as shown, or can be integral with the frame 110. The body portion 120 may have a surface with edges, ridges or material to help the user grip the body portion 120.

External Pressure Member 150

Referring to FIG. 4, external pressure members 150 are attached to the distal end portion 115 of the frame member 110. For instance, the external pressure members 150 may be nasal pinch pads, such as soft material made of silicone or other soft material to apply constant no-slip pressure to the soft part of the nose on either side. As shown, the pads 150 may have a main body 152 that is substantially circular in shape and contoured, and an optional upper ledge 154. The ledge 154 projects upward and forward (with respect to the embodiment of FIG. 2) to extend toward the top of the user's nose. The main body 152 is configured to evenly disperse constant pressure to the sidewalls of the nose. And the upper ledge 154 may provide support to a nasal icepack.

The pad 150 is sufficiently thick and soft to be comfortable to a user, but also to apply sufficient pressure to the nose to stop bleeding. The pad 150 can be molded directly to the distal end portion 115 of the frame 110, and may surround the reverse bend 116, cross-member 118, and/or distal end 119. In an alternative embodiment, the pad 150 can have an internal opening that has a shape which matches the distal end portion 115 of the frame 110. Accordingly, the user can removably attach the pad 150 to the distal frame portion 115 by sliding the distal frame portion 115 into the opening inside the pad 150. The opening can be located in the main body 152 as well as the ledge 154, to fully receive the reverse bend 116, cross member 118 and bent distal end 119. The ledge 154 is provided at the same bend as the distal end 119 to match the shape of the distal end 119. Of course, other suitable connections can be provided between the pad 150 and the frame 110. For instance, the pad 150 can be adhered, strapped or fastened to the frame 110, and no opening or recess need be provided in the pad 150.

The pad 150 is soft and malleable so that it conforms to the shape of the nose. Thus, pressure may be controlled by the force exerted by the user to apply enough pressure to stop bleeding but the user can control the force to gage for comfort. The pad 150 and the entire clip 100 can be made in various dimensions to fit an adult, child or different sized noses.

Internal Pressure Members 170

Referring to FIG. 4, a set of two internal pressure members 170 are provided and each attach to the clip mechanism 120. Each of the internal pressure members has a base portion 172 and a main body portion 174. A central elongated hole or receptacles extends into the base 172. The hole is configured to be slightly larger than the prongs 120 on the clip mechanism 120. The hole slidably receives one of the respective prongs 120 and forms a friction fit therewith. The friction fit prevents the internal pressure member 170 from inadvertently sliding off of the prong 129, but allows the internal pressure member 170 to be removed and replaced from the clip mechanism 120 after use.

The main body portion 174 extends outward at an angle (upward in FIG. 1) with respect to the base 172. As best shown in FIGS. 3(c), 5, 6, the main body 174 extends in a direction substantially orthogonal to that of the ledge 154 of the external pressure member 150. Thus, the main body 174 can enter the internal nose of a person, while the ledge 154 extends up along the outer lateral surface of the person's nose. The main body portion is tapered to be larger at the base 172 and narrowed at the distal end, which may also be rounded, to form a general cone shape. As best shown in FIG. 3, an inside side edge 176 of the sponge is relatively straight, whereas the outer side edge 178 is angled inward. Thus, the two internal pressure members 170 are each configured to be shaped and sized to fit in a person's nose. The internal pressure members 170 are inserted into each nare before the device 100 (i.e., the side portions 114 and pads 150) is pinched in place. The sponges 170 are sufficiently large to exert an inward pressure against the internal parts of the nose, including the ant septum, to facilitate stopping of the bleeding by causing a tamponade.

In one exemplary embodiment, the internal pressure member 170 may be a nasal sponge insert and can be made for instance of foam, sponge, dehydrated sponge like materials, and can optionally be presoaked with medication (and optionally dehydrated). They can be biocompatible foam that absorbs blood and/or induces clot formation or hemostasis. The sponges can expand to further exert a pressure against the nose to stop bleeding. In addition, the nasal sponges 170 may be made out of absorbable polymers or other absorbable material with zinc oxide, bacitracin or antibiotic ointment in addition to analgesic and vasoconstrictive medications such as but not limited to oxymetazoline, epinephrine, phenylephrine, pseudoephedrine, lidocaine or tranexamic acid (TXA).

As shown in FIG. 1, the main body 174 of the sponge 170 extends upward upon entry and then posterior into the nare, while the base 172 may project slightly out of the nasal passage at the exterior of the nose. The nasal sponges 170 fit securely below nose but above the level of the upper lip to be comfortably positioned in the nasal passages, and can be readily inserted into and withdrawn from the nasal passages. The sponge 170 can easily slide into the nare and quickly and easily release pre-soaked medication to mucous membranes inside the nasal shaft. They do not adhere to or disrupt scab formation. The sponges 170 can be provided in different sizes, shapes and angles to fit different ages (nose size) and internal nose shapes.

Overall Operation

The frame member 110 may form two positions for the device 100: an open position (FIG. 3(a)) and a closed or pinch position (FIGS. 3(b), 3(c)). In the open position (FIG. 3(a)), the side frame portions 114 may be substantially orthogonal or at an obtuse angle with respect to the middle portion 112 (though in some embodiments the side frame portions 114 can be slightly smaller than orthogonal). Thus, the distal ends 115 are wider apart than the user's nose so that the user can insert the nasal sponges 170 into the user's nasal passages by moving the side frame portions 114 upward (and posteriorly) along the external lateral side surface of the user's nose. The open position is the normal position for the device when it is at rest.

Once the device 100 is in the proper position on the nose, the user can then bend the side portions 114 inwardly to the pinch position. In the pinch position (FIG. 3(b), (c)), the side frame portions 114 are positioned inward so that the distal end portion 115 is narrower than the normal width of a user's nose. In that position, the side frame portions 114 are at an acute angle with respect to the middle portion 112. The side frame portions 114 remain in that position and applies an inward pinch force against the user's nose to help stop the nosebleed. The side frame portions 114 remain in that pinched position until separated by the user for removal from the nose.

As shown in FIGS. 1 and 2, the central portion 112 of the frame member 110 is intended to be positioned at the patient's upper lip directly below the nostrils and septum. The side frame portions 114 extend upward on the patient along the lateral surface of the nose. The distal end frame portions 115 are positioned at the lateral surface of the nose, so that the external pads 150 apply pressure at a proper position to stop the nosebleed. The side frame portions 114 exert an inward force so that the nasal pads 150 apply an inward pressure or pinch force against the lateral surface of the nose. The nasal pads 150 thereby apply pressure to the ala (soft side walls of the nose). The pinch force can be controlled by adjusting the amount of inward bias of the side portions 114, so that enough force is applied to control the bleeding, but without exerting too much force to cause pain or damage the user s nose.

As shown, once the device 100 is positioned on the nose, it is hands-free since it remains in place on the user's nose by itself due to the inward pinch force once the side portions 114 are bent to the inward pinch position, and without the user having to hold it in position. The device 100 remains in position until the user separates the side portions 114 and then withdraws the nasal sponges 170 from the user's nasal passage. Thus, the device 100 (i.e., distal end portions 115 and pads 150) pinches the lateral side surfaces of the user's nose, and simultaneously stops bleeding through delivery of vasoconstrictive medications applied by the nasal sponges 170. Of course, the device 100 need not have both the pads 150 and the nasal sponges 170. For instance, the sponges 170 (and body portion 120) can be removed, so that only a pinching force is applied by the distal end portion 115 and pads 150.

In an alternative embodiment of the invention, the frame member 110 may be inwardly biased, whereby the side portions 114 are positioned inwardly (FIGS. 3(*b*), 3(*c*)) when at rest and may be separated outwardly by the user to be in the open position. In the open position, the device 100 may be placed over the user's nose, and when the user releases the side portions 114, they return to the inward position to apply a pressure to the nose.

According to this alternative embodiment, the pinch position may be the normal position for the device 100 when it is at rest. To place the device 100 on the user's nose, the device 100 is moved to the open position whereby the side frame portions 114 are forced apart against the inward bias force. That can be performed, for instance, by pulling outward on the side portions 114 and/or the nasal pads 150. The nose sponges 170 are then positioned inside the user's nasal passage and the nasal pads 150 are simultaneously positioned along the exterior lateral surface of the nose. The side frame portions 114 are then released, so that they move inward and return to the pinch position (FIG. 3(*b*)). In that pinched position, the nasal pads 150 exert a pinching force. In the open position, the side frame portions 114 can be at an acute angle, or more preferably at an orthogonal or obtuse angle with respect to the middle portion 112.

The vast majority of nosebleeds occur in the anterior part of the nose and from the nasal septum. This area contains many blood vessels from Kiesselbach's plexus, also known as Little's area. The nasal compression device 100 is designed to control bleeding via direct compression on the outer nose, by placing pressure directly over Kiesselbach's plexus, in combination with vasoconstriction from sponge inserts soaked with oxymetalozine or other vasoconstricting medication or hemostatic agent possible with some analgesic ingredient such as lidocaine and/or antibacterial agent such as bacitracin. The device 100 may also be designed to come in multiple sizes to fit adults and children.

The device can be made available in several sizes, such as child, teen, and adult. Each size may have, for instance, a different width (e.g., by varying the length of the central portion 112), a different height (e.g., by varying the length of the side portions 114), and/or a different inward pinch force (e.g., by varying the inward bias of the side portions 114). The different sizes can also have different sizes of nasal pads 150 and nasal sponges 170.

Ice Pack

Figure 8:
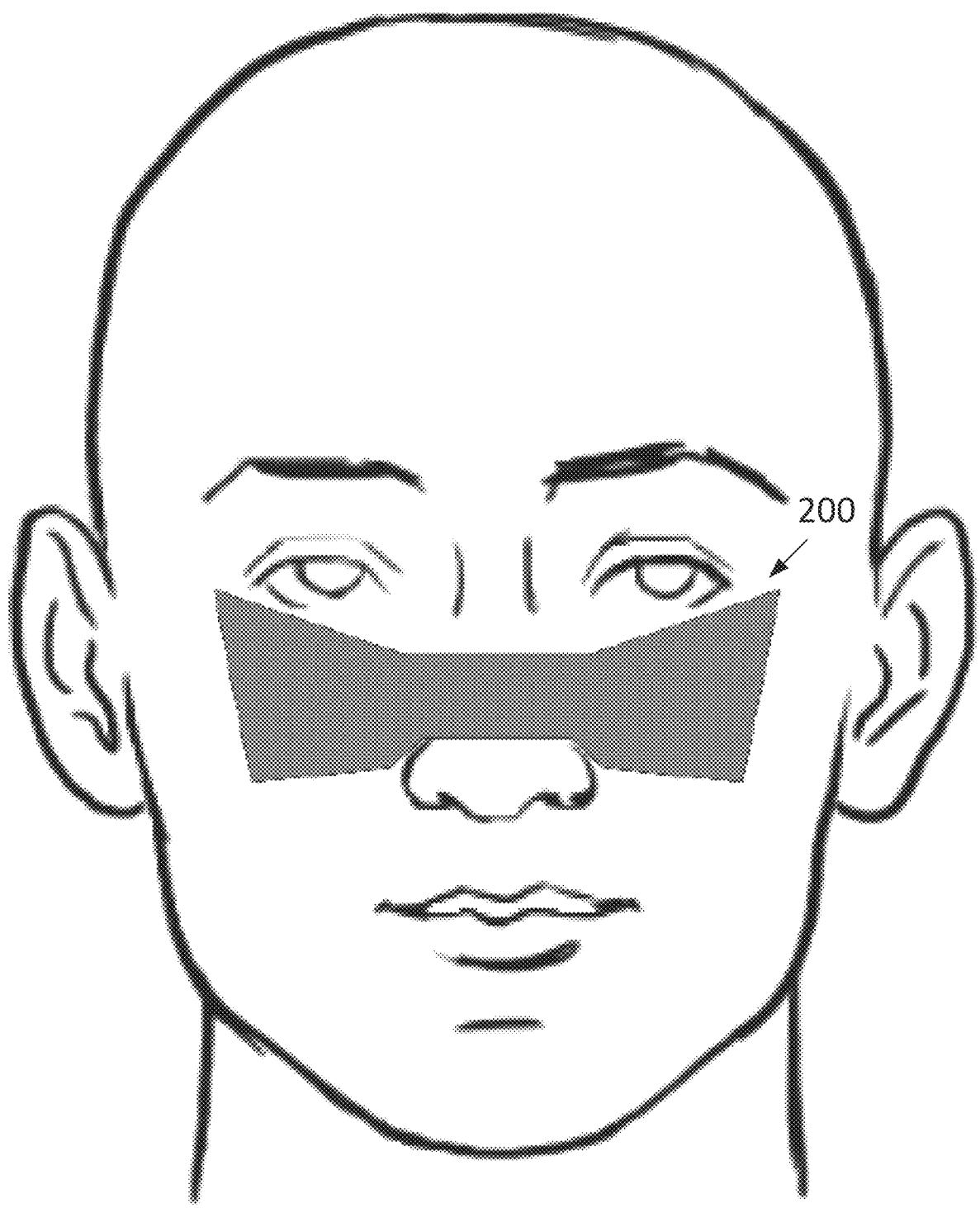
FIG. 8 is a front view of an ice pack positioned on a user in accordance with another aspect of the invention.
Figure 9:
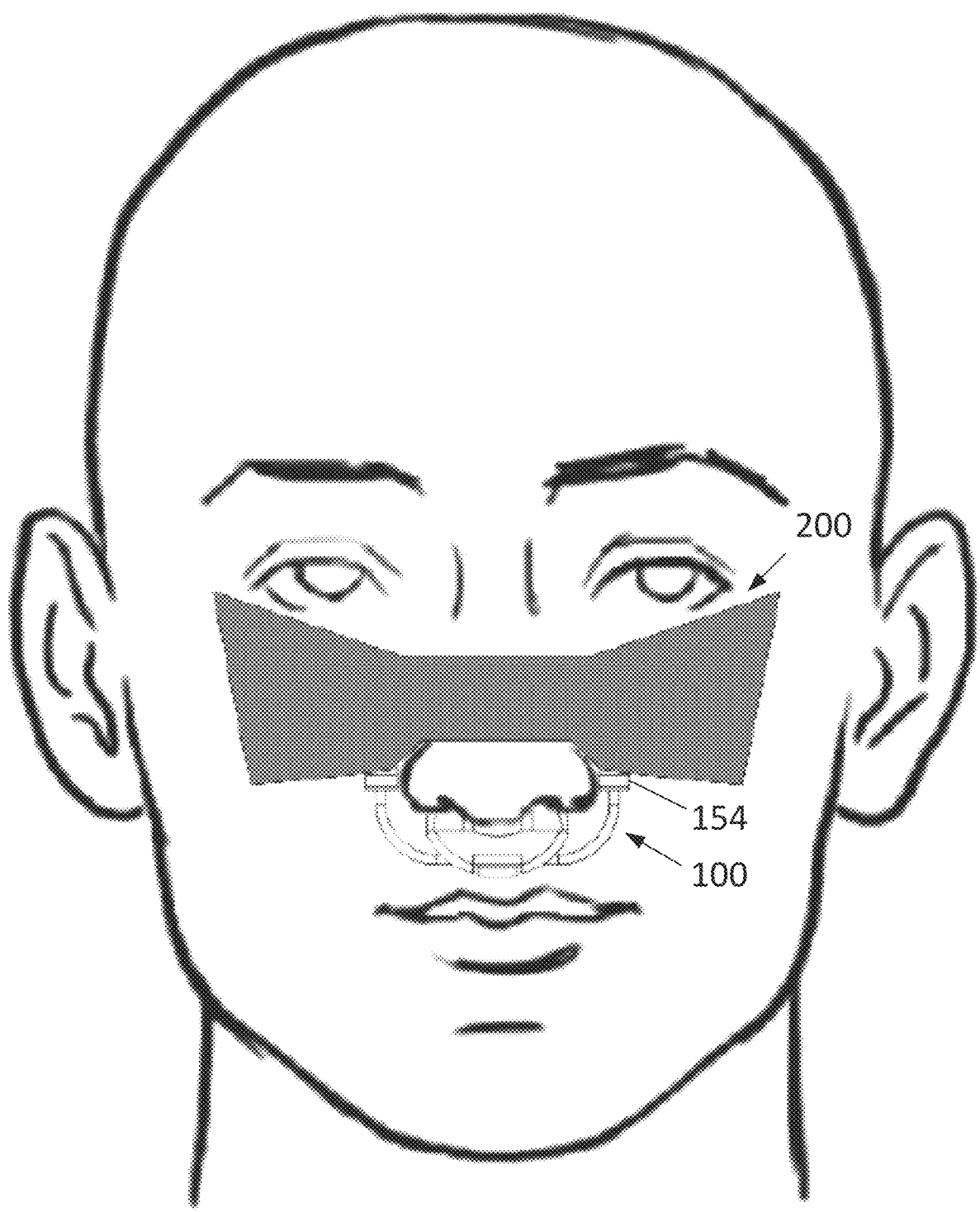
FIG. 9 is a view of the ice pack and compression device used together.

Turning to FIGS. 8-11, an ice pack assembly 200 may optionally also be provided in accordance with a non-limiting illustrative embodiment of the invention. As shown in FIG. 9, the ice pack 200 may be utilized together with the nasal compression device 100 of FIGS. 1-7 (or with a different nasal compression device). Or as shown in FIG. 8 the ice pack 200 may instead be utilized by itself separate from and without the nasal compression device 100. Likewise, the nasal compression device 100 can be utilized by itself separate from and without the ice pack 200 (or with a different ice pack). When used in combination with the nasal compression device 100, the combination of compression (by the frame 110 and pads 150), medication (applied by the sponges 170), and cooling (by the ice pack 200) together facilitate treatment of the nosebleed.

In one illustrative non-limiting embodiment of the invention, the ice pack assembly 200 has two primary ice pack layers or sheets 210, 250. The first and second layers 210 have the same exact size and shape as each other. Each are each elongated and have a middle portion 212, 252 and two end portions 214, 254 that are at opposite ends of the middle portion 212, 252 so that the middle portion 212, 252 is positioned between the two end portions 214, 254, respectively. The middle portion 212, 252 is generally rectangular in shape and has a smaller width than the end portions 214, 254. The end portions 214, 254 are formed as wings that are tapered outward from the middle portion 212, 252, so that the first and second layers 210, 250 (as well as the overall ice pack assembly 200) each have a general bow-tie shape. The first and second layers 210 each have an inner surface 216, 256 that faces toward the user (when the assembly 200 is applied to the user), and an outer surface 218, 258 that faces away from the user (when applied).

The shape enables the assembly 200 to extend across the user's nose, above the lips and below the eyes. More specifically, as shown in FIGS. 8-9, the middle portion 212, 252 extends across the bridge of the user's nose, along the outer lateral sides of the nose. And the side portions 214, 254 reach opposite cheeks of the user's face.

Figure 11:
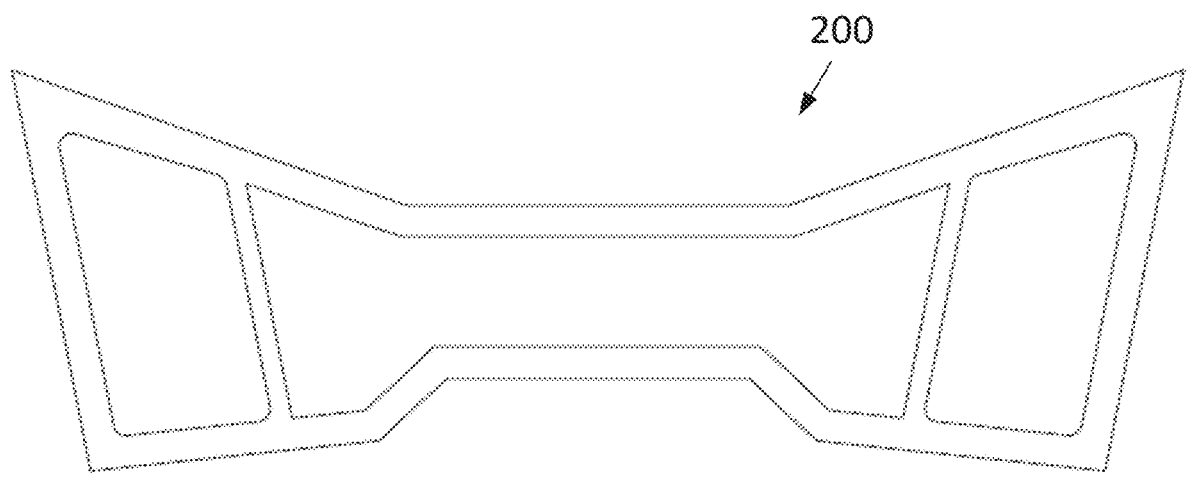
FIG. 11 is a detailed view of the ice pack.

The first ice pack layer 210 is closest to the user when the ice pack assembly 200 is applied to the user. An adhesive layer 220 is applied to the inner surface 216 of the first layer 210. The adhesive layer has the same general shape as the first and second layers 210, 250, with a middle portion 222 and an end portion 214. But the adhesive layer 220 is smaller than and has a smaller outer periphery than the first and second layers 210, 250, as shown in FIG. 11. In addition, the end portion 224 may be split or divided into an inner end portion 224*a* and an outer end portion 224*b* as shown, which allows for greater flexibility and ease of handling.

The adhesive layer 220 has an inner surface 226 that faces toward the user, and an outer surface 228 that faces away from the user. The outer surface 228 is adhered to the inner surface 216 of the first layer 210. A plastic film 229 is a polyurethane film that is permanently attached to the inner surface 226 of the middle portion 222, which in turn is connected to the middle 212 of the layer 210. The plastic film 229 slightly reduces the cold against the bridge of the nose. The ends 224 have an adhesive, such as a gentle tape, that adhere to the skin so that it can reliably attach to the person and be easily removed following treatment. The adhesive layer 220 (and ice pack assembly 200) can then be placed on the user so that the ice pack assembly 200 is adhered to the user's face. The adhesive layer 220 may be coated with any suitable adhesive that holds the ice pack 200 in place on the user's face and can be readily removed, such as a gentle tape.

The first and second layers 210, 250 are sealed together to form a pocket. For instance, the outer peripheral edge of the layers 210, 250 can be heat sealed together to form a pocket therebetween. A material may be added to the pocket that creates cold, such as ammonium nitrate or urea. The material may be added, for instance, after 3 sides of the layers 210, 250 are sealed together. After the cooling material is added, the final side can be heat sealed so that the layers 210, 250 form a complete enclosure.

Figure 10:
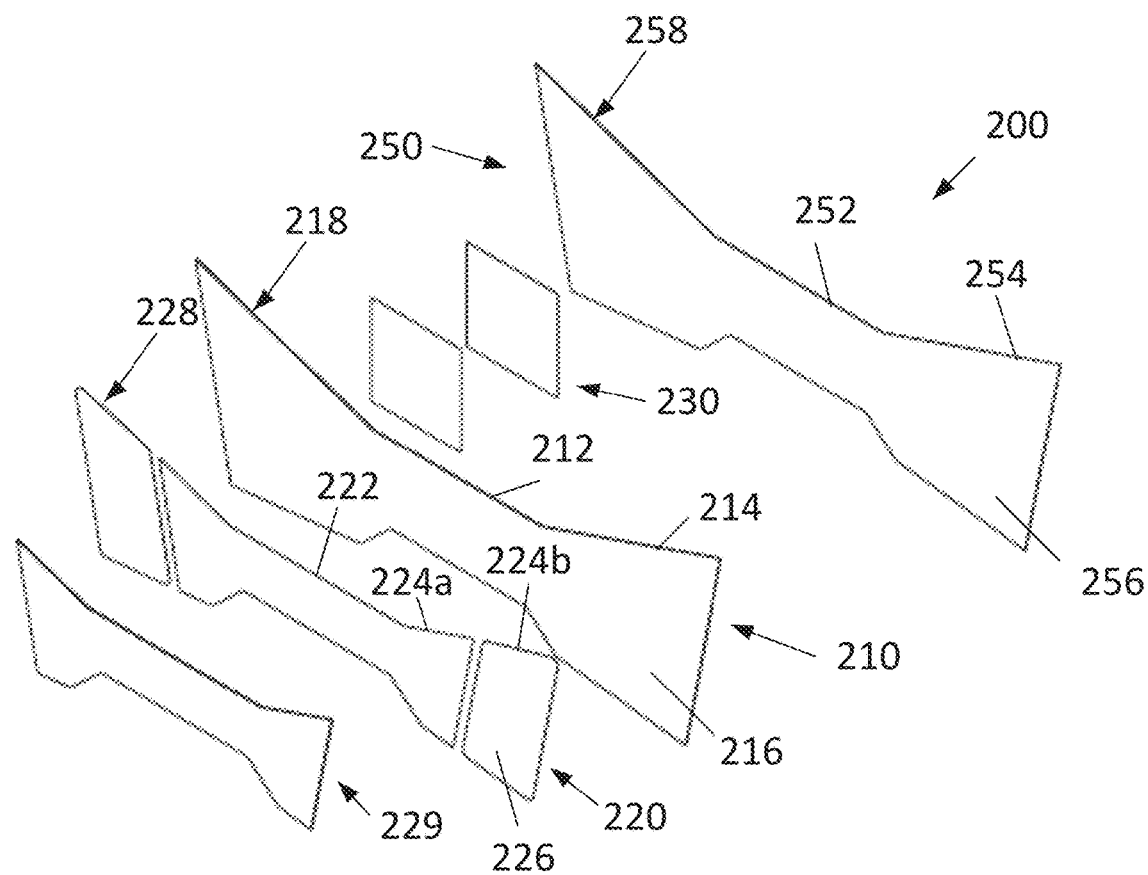
FIG. 10 is an exploded view of the ice pack.

In addition, a water pouch 230 may be provided in the pocket. More particularly, the pouch 230 can be in the large pocket, i.e. sandwiched between the outer surface 218 of the first layer 210 and the inner surface 256 of the second layer 250 before they are sealed together (or after 3 sides have been sealed together). The pouch 230 is a small enclosure that retains water. In the embodiment of FIG. 10, two sheets 230 are shown; those can be sealed together at the peripheries with the cold-retaining material therebetween. For instance, the two sheets may be made of plastic and are heat sealed together to form a single pouch 230 with water contained in the pouch 230 formed between the two sealed sheets. Once the ice pack assembly 200 is ready to use, the user squeezes the water pouch 230 to break the pouch 230 and release the water into the surrounding ammonium nitrate in the large pocket (formed between layers 210, 250). That reaction causes the mixture to get cold. The assembly 200 can then be placed on the user by adhering the adhesive layer 220 to the user.

It will be appreciated that alternative methods for providing a cold ice pack assembly 200 can be utilized. For instance, water or other material that retains the cold can be added to the pocket created by the two layers 210, 250; and the small pouch 230 need not be provided. The entire assembly 200 can then be placed in a refrigerator or freezer to cool or freeze the material in the pocket, so that it is cold and ready for use.

As shown in FIGS. 8-9, the ice pack assembly 200 is configured to apply cold across the nasal bridge and checks of the user for the requisite period of time (at least 10-20 minutes), without obscuring the user's vision. The ice pack may have a colorimetric indicator, such as a liquid crystal thermometer that changes color when cold and back to a different color when warm indicating a relative time that the device should be left in place before checking for bleeding, approximately 10-15 minutes.

It will also be appreciated that the adhesion layer 220 need not be provided. Instead, the assembly 200 can be provided with an elastic band that connects to the side edges of the assembly 200. The elastic band can extend around the user's head to hold the assembly 200 to the user's face. Still other techniques can be utilized, such as VELCRO® straps.

Figure 12:
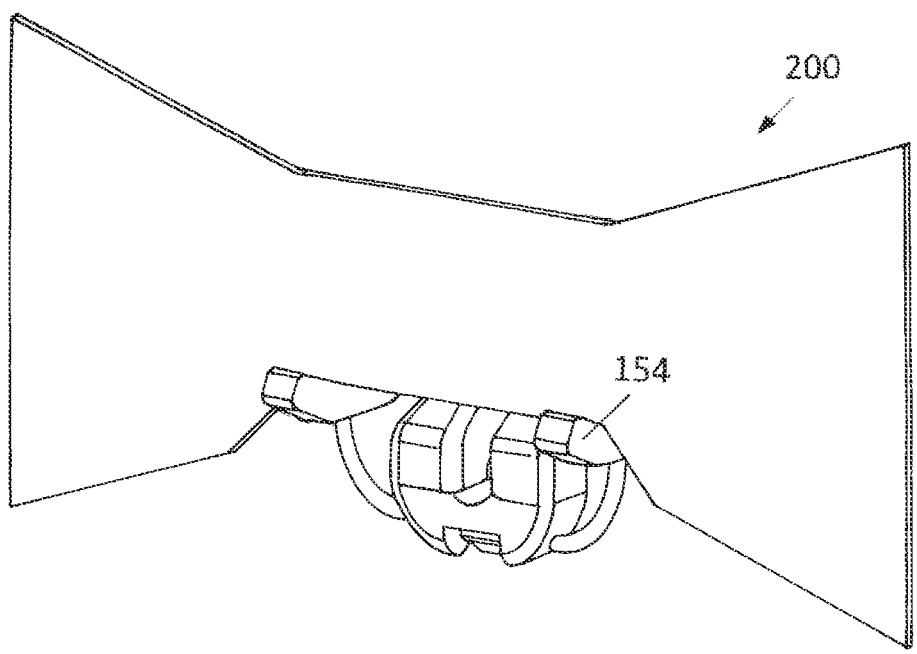
FIG. 12 is a detailed perspective view of the compression device and ice pack.

With reference to FIG. 12, the ice pack 200 is shown in use with the nasal compression device 100. As illustrated (see also FIG. 9), the nasal compression device 100 may be designed to hold and support the facial instant ice pack 200 across the nasal bridge and cheeks without obscuring any part of the visual profile. The ice pack can be placed across the nasal bridge and supported by the upper edge of the main body 152 and the ledge 154 of the nasal pinch pads 150, as well as the adhesive material that holds the icepack to the outer cheeks.

The cooling affect by the ice pack 200 can shape the compression device 100 and serve as a timer. By using smart polymer materials (such as the temperature responsive polymer Poly(N-isopropylacrylamide)) for the frame 110 (such as at the bend 113 between the central portion 112 and the side portions 114), the compression device 100 could be placed in the pinched position. For instance, the polymer material could straighten at the bends at a temp range of about 50 degrees. Thus, as the ice pack warms over about 15 minutes, it would change the temperature of the device 100 metal and the polymer materials would begin to straighten, reducing the pinch and signaling the time to remove the device.

The ice pack assembly 200 may also have an outer lining that is contoured to the nasal ice pack and shaped to fit comfortably below the eyes, over the nasal bridge and extend over the maxilla. An inner icepack lining may also be provided as a comfort barrier with polyurethane film to sit directly over nose and face to prevent over cooling. The ice pack may come in different size to fit children and adults of various dimensions.

Nosebleed Kit

The nasal compression device 100 and/or the ice pack 200 can be packaged with other nosebleed accessories. Thus, a kit can be provided that includes two or more of the following: compression device 10X), ice pack 200, bib 300, medication, and timer.

Figure 13:
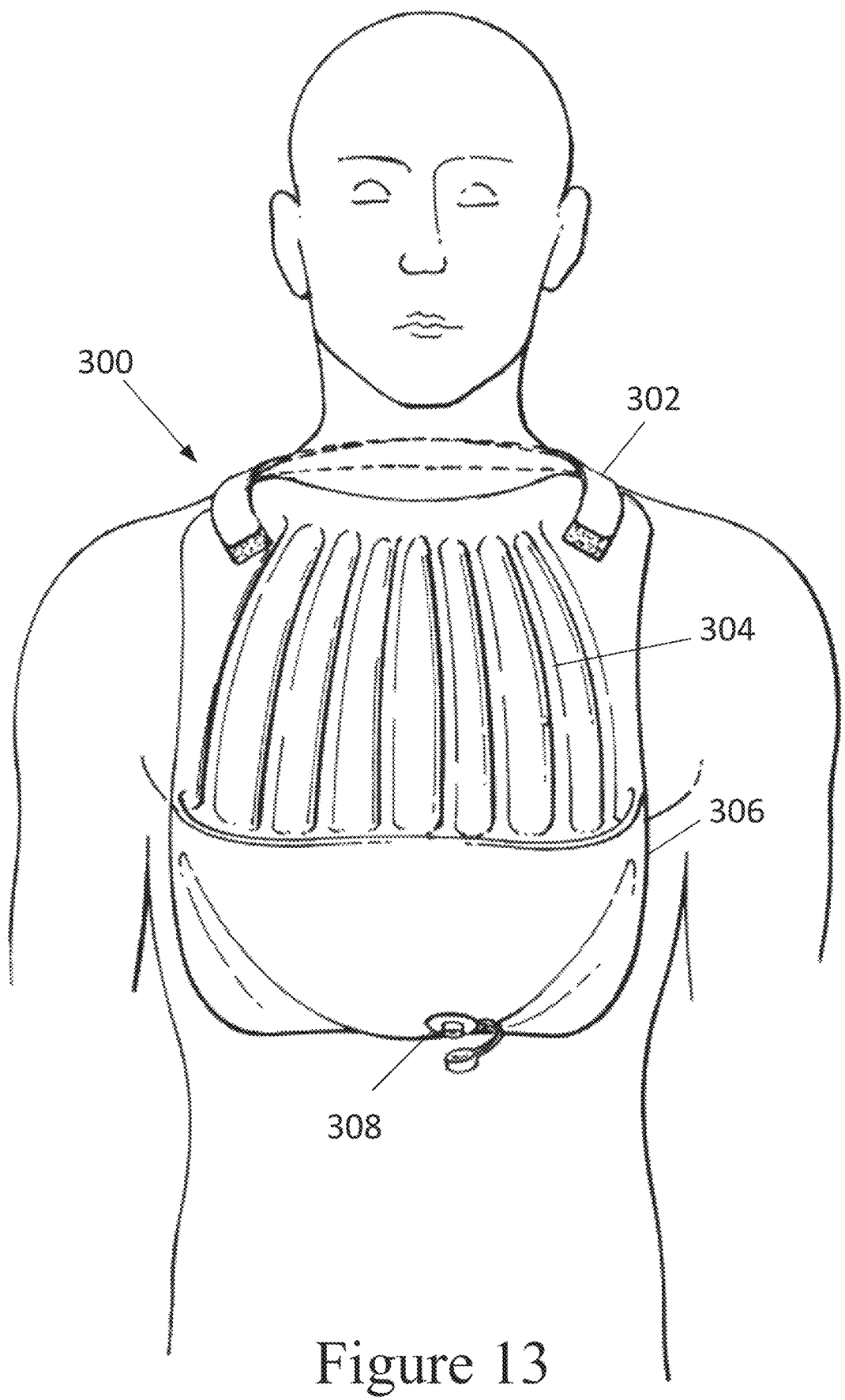
FIG. 13 is a view of a bib positioned on a user in accordance with another aspect of the invention.

A plastic or absorbent bib 300 is shown in FIG. 13. The bib 300 may provide protection from blood and body fluids. The bib attaches around the neck via a fastener 302 (such as Velcro, button, tie or adhesive). The bib 300 has a pocket 306 at its bottom to catch run off liquid or bodily fluids that can be drained from the corner of the bib via a re-sealable hole 308 (or a valve or opening). One or more grooves or drainage channels 304 can extend along the entire length (or portion of the length) of the bib 300 to direct fluids into the pocket 306. The bib 300 can be a plastic or cloth material with enough surface area to cover patient's chest and collect blood and bodily fluids into a pocket that has a sealable hole in the corners for drainage.

The medication can include chemical vasoconstriction (oxymetalzoline, neosynephrine, epinephrine, phenylephrine, cocaine, TXA, other hemostatic agent), chemical absorptive polymer, or analgesia such as lidocaine. The medication can be in the form of a powder, gel, liquid, and can be impregnated on a sponge (such as the nasal sponge 170) or a sealed packet for one time use. The timer assists the user to maintain pressure for adequate time (10+ min). For instance, the timer may be a liquid crystal thermometer strip that changes color based on temperature change of cooling pack, or other electronic or simple timer mechanism can be used.

Conclusion

The device 100 provides a safe, effective and low-cost solution to nosebleed emergencies. The device comes in adjustable sizes and applies constant hands-free pressure to the soft side walls of the nose, incorporates cooling to help constrict vessels to control bleeding, and is designed to automatically apply adequate pressure to the nose for the appropriate amount of time so users know when to remove the device to check for bleeding. The invention can also utilize medication that further controls bleeding by constricting bleeding vessels and improves the success of hemorrhage control.

The present invention provides value to three different customer segments: medical providers, sports medicine professionals and parents, caretakers or individuals who suffer from frequent nosebleeds. For medical providers, this device can reduce the time needed by medical professionals to effectively manage common nosebleeds. For coaches, trainers and school nurses, this device is easy to use and effective for nosebleed emergencies. For parents and caretakers, the invention is the comfortable, safe, low-cost solution to nosebleed rescue that can reduce or eliminate costly visits to the emergency room or doctor's office.

The invention is available in adjustable sizes and applies constant hands-free pressure to the soft side walls of the nose, incorporates cooling to help constrict vessels to control bleeding, and is designed to automatically apply adequate pressure to the nose for the appropriate amount of time so consumers know when to remove the device to check for bleeding. The invention also uses medication that further controls bleeding by vasoconstriction and improves the success of hemorrhage control.

The invention is a safe, effective and simple to use device that be placed on the patient by a nurse or even a family member and does not require constant supervision by a medical professional. It allows providers to effectively manage epistaxis with minimal cost, time or repeated attempts and helps to facilitate throughput which reduces length of stay, an important hospital benchmark. These advantages make the present invention attractive not only to the beneficiary, the patient, but also to the hospital or physician who recommends use of the product.

The invention is easy to use, stops bleeding immediately and has step-by-step instructions for managing nosebleeds. It is a device that any trainer or first aid station would want to have on hand for disposable, immediate and effective treatment for nosebleed emergencies. Any customers who are prone to nosebleeds would be attracted to the low price, intuitive design, effectiveness and comfort. The device provides easy step-by-step instructions to apply constant pressure to the correct part of the nose with the added value of including cooling and medication which increases the success of bleeding control and potentially prevents unnecessary visits to the doctor's office or emergency room. Currently, there are no devices on the market that use this combination of technique and medication to treat nosebleed emergencies. The invention is valuable because it provides cost savings, effective management and ease of use to (1) medical providers/physicians, (2) school and sports professionals and (3) direct to consumer customer segments and by preventing prolonged nosebleeds it avoids overutilization and expense to the health care system.

The device 100 is adjustable for comfortable fit to the contour of the nose, since the nasal pads 150 are soft and malleable and with applied pressure conforms to the shape of the nose. It applies the appropriate amount of pressure in the appropriate location at the soft side walls of the nose, hands-free. It is positioned completely below or to the side of the nose, and does not extend upward above the soft side walls of the nose. Thus, it does not obstruct vision or line of sight of the user's eyes. It also does not extend below the upper lip, so that it does not obstruct the user's mouth.

It is noted that the device 100 as shown and described is configured for simultaneous use on both nostrils. However, the device 100 can be configured so that only one nostril is treated, such as by providing one internal pressure member 170 and one respective external pressure member 150.

The description uses several geometric or relational terms, such as curved, orthogonal, circular, rounded, straight, and tapered. In addition, the description uses several directional or positioning terms and the like, such as top, bottom, and side. Those terms are merely for convenience to facilitate the description based on the embodiments shown in the figures. Those terms are not intended to limit the invention. Thus, it should be recognized that the invention can be described in other ways without those geometric, relational, directional or positioning terms. In addition, the geometric or relational terms may not be exact. For instance, elements may not be exactly perpendicular to one another but still be considered to be substantially perpendicular because of, for example, roughness of surfaces, tolerances allowed in manufacturing, etc. And, other suitable geometries and relationships can be provided without departing from the spirit and scope of the invention.

Within this specification embodiments have been described in a way which enables a clear and concise specification to be written, but it is intended and will be appreciated that embodiments may be variously combined or separated without departing from spirit and scope of the invention. For example, it will be appreciated that all preferred features described herein are applicable to all aspects of the invention described herein.

The foregoing description and drawings should be considered as illustrative only of the principles of the invention. The invention may be configured in a variety of shapes and sizes and is not intended to be limited by the preferred embodiment. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

The invention claimed is:

1. A nose compression device for a nose of a living being, the device comprising:
   a malleable frame having a middle section and two side sections angled with respect to the middle section to apply an inward compression against an outside of the living being's nose, wherein the two side sections are flexible and moveable between an open relaxed position where the two side sections are outward, and a pinch position where the two side sections are moved inward with respect to the middle section, and wherein the open relaxed position does not have any outward/inward force;
   a body assembly attached to the middle section of said malleable frame, said body assembly having a main body with a clip; and
   two nasal sponge-like or hemostatic material attached to one or more prongs of the body assembly and configured for insertion into the living being's nasal passages, whereby the clip removably attaches to the malleable frame to obtain a desired position of the two nasal sponge-like or hemostatic material with respect to the living being's nose.

2. The device of claim 1, wherein the middle section can be positioned below the living being's nose and the two side sections extend upward along opposing lateral side surfaces of the living being's nose.

3. The device of claim 1, said main body having a front end and a rear end, said one or more prongs extending outward from the rear end of said main body and a clip mechanism located at the front end of said main body, said clip mechanism removably coupling said main body to said malleable frame.

4. The device of claim 1, wherein each of said side sections have a distal end, and further comprising a malleable pad attached to the distal end.

5. The device of claim 4, wherein the pad extends upward along the lateral surface of the living being's nose.

6. A nose compression device for a nose of a living being, the device comprising:
   a malleable frame having a middle section and two side sections angled with respect to the middle section to apply an inward compression against an outside of the living being's nose;
   a body attached to the malleable frame; and
   two nasal sponge-like or hemostatic material attached to the body and configured for insertion into the living being's nasal passages;
   wherein each of said side sections have a distal end, and further comprising a pad attached to the distal end, and the distal end has a U-shaped reverse bend.

7. The device of claim 1, further comprising two prongs extending outward from said body, each of said two prongs receiving a respective one of said two nasal sponge-like or hemostatic material.

8. The device of claim 1, wherein said two nasal sponge-like or hemostatic material contain a medication.

9. The device of claim 8, wherein the medication is a vasoconstrictive medication and/or an analgesic medication, and/or an antibacterial agent.

10. The device of claim 8, wherein the medication comprises one or more of oxymetazoline, epinephrine, phenylephrine, pseudoephedrine, lidocaine, tranexamic acid, lidocaine, zinc oxide, and bacitracin.

11. The device of claim 6, wherein the two side sections are orthogonal or obtuse with respect to the middle section in an open relaxed position which the two side sections are outward.

12. The device of claim 1, wherein the device does not obstruct the living being's eyes or mouth.

13. The device of claim 1, further comprising an ice pack applied over the compression device, said ice pack cooling the living being's nose.

14. The device of claim 6, said two nasal sponge-like or hemostatic material each having a medication and configured to apply the medication to an inside of the living being's nose.

15. The device of claim 1, wherein the nasal sponge-like or hemostatic material have a distal end and a proximal end and are tapered to be larger at the distal end and smaller at the proximal end.

16. Tire device of claim 13, wherein said ice pack is coupled to said compression device.

17. The device of claim 1, wherein the middle section is substantially straight.

18. A nosebleed compression kit comprising:
the nose compression device of claim 1;
an ice pack applied over the compression device; and
a bib having a chest portion for extending over a chest of the living being, said bib further having a pocket for receiving blood from the living being's nose via the chest portion, and drainage channels in the chest portion for guiding the blood into the pocket.

19. The kit of claim 18, further comprising a timing mechanism.

20. The kit of claim 19, wherein the timing mechanism comprises a color change time indicator on said ice pack.

21. A nose compression device for a nose of a living being, the device comprising:
a malleable frame having a middle section and two side sections angled with respect to the middle section to apply an inward compression against an outside of the living being's nose;
a body attached to the malleable frame;
two nasal sponge-like or hemostatic material attached to the body and configured for insertion into the living being's nasal passages; and
an ice pack applied over the compression device, said ice pack cooling the living being's nose.

22. A method of using a nose compression device for a nose of a living being, the method comprising:
applying an inward compression against an outside of the living being's nose by using a nose compression device having a frame with a middle section and at least one side section angled with respect to the middle section, the at least one side section applying the inward compression; and,
inserting a nasal sponge-like or hemostatic material into the living being's nasal passage, the nasal sponge-like or hemostatic material attached to a body that is attached to the middle section of the frame.

23. The method of claim 22, wherein the applying an inward compression is simultaneous with inserting the nasal sponge-like or hemostatic material.

24. The method of claim 22, further comprising applying a medication to the nasal sponge-like or hemostatic material.

25. The method of claim 24, wherein the medication comprises a vasoconstrictive, and/or an analgesic medication and/or antibacterial medication.

26. The method of claim 22, further comprising applying an ice pack over the nose compression device.

27. The method of claim 22, wherein the nasal sponge-like or hemostatic material is premedicated.

28. The device of claim 6, each of said side sections further comprising a proximal end having a side section, the side section coupled to the U-shaped reverse bend, and further comprising a cross-member attached to the reverse bend, the cross-member crossing the side section, whereby each of said side sections form a closed oblong shape.

29. The device of claim 28, further comprising a substantially orthogonal bend coupling the middle section to each of the two side sections.

30. The device of claim 1, wherein the main body is configured to be positioned entirely below the living being's nose, and one or more prongs extending outward from the main body.

31. The device of claim 1, wherein the malleable frame comprises a wire.

32. The device of claim 1, wherein the malleable frame comprises a shape memory material.

* * * * *